United States Patent

Arcamone et al.

[11] 4,098,884
[45] Jul. 4, 1978

[54] DOXORUBICIN THIOESTERS

[75] Inventors: Federico Arcamone; Luigi Bernardi; Bianca Patelli, all of Milan, Italy

[73] Assignee: Societa' Farmaceutici Italia S.p.A., Milan, Italy

[21] Appl. No.: 776,821

[22] Filed: Mar. 10, 1977

[30] Foreign Application Priority Data

Mar. 30, 1976 [GB] United Kingdom ............ 12701/76

[51] Int. Cl.$^2$ .................... A61K 31/65; C07H 15/24
[52] U.S. Cl. ........................ 424/180; 536/4; 536/17; 536/121
[58] Field of Search ............... 536/4, 17, 121; 424/180

[56] References Cited

U.S. PATENT DOCUMENTS

| 4,024,224 | 5/1977 | Arcamone et al. | 536/17 |
| 4,031,211 | 6/1977 | Patelli et al. | 536/17 |
| 4,035,566 | 7/1977 | Israel et al. | 536/17 |

OTHER PUBLICATIONS

Pigman, "The Carbohydrates", 1957, Academic Press Inc., New York, N. Y. p. 160.

*Primary Examiner*—Johnnie R. Brown

*Attorney, Agent, or Firm*—Hubbell, Cohen, Stiefel & Gross

[57] ABSTRACT

Doxorubicin thioesters of the formula

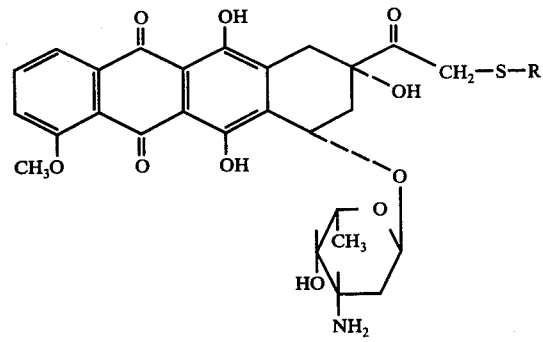

wherein R is acyl and which are useful in treating animal tumors, are prepared by reacting 14-bromo-daunomycin with a salt of a thioacid of the formula RSM wherein R is as defined above and M is an alkali metal atom or a quaternary ammonium salt in an inert polar solvent. The invention described herein was made in the course of work under a grant from the Department of Health, Education, and Welfare.

11 Claims, No Drawings

DOXORUBICIN THIOESTERS

CROSS REFERENCE TO RELATED APPLICATIONS

None.

BACKGROUND OF THE INVENTION

The present invention relates to novel derivatives of doxorubicin, and processes for their preparation. The starting material for the preparation of these novel derivatives is 14-bromodaunomycin which is fully described in U.S. Pat. No. 3,803,124, owned by the assignee hereof.

SUMMARY OF THE INVENTION

The present invention, in one aspect thereof, is concerned with certain novel derivatives of doxorubicin, and specifically, a new class of doxorubicin thioesters having the following structural formula

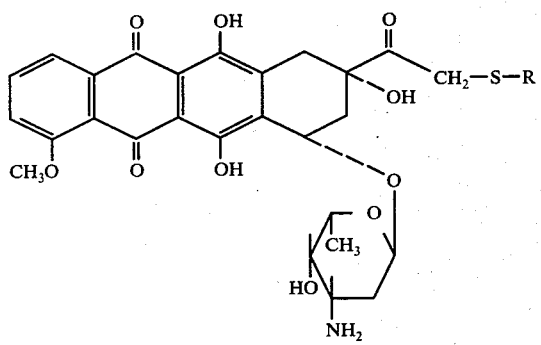

wherein R is the acyl radical of an aliphatic carboxylic acid having 2 to 8 carbon atoms, benzoic acid, nicotinic acid or pyrazinoic acid. When R is the acyl radical of an aliphatic acid, it is preferably, acetyl, propionyl, butanoyl or octanoyl.

In another aspect, the present invention relates to a method for preparing the compounds of the invention. According to the method of the invention, these doxorubicin thioesters are prepared by reacting 14-bromodaunomycin with a salt of a thioacid. More particularly, in accordance with the method of the invention, 14-bromodaunomycin is reacted with a compound of the formula RSM, wherein R is as defined above and M is an alkali metal or a quaternary ammonium radical.

The reaction is carried out in the presence of an inert polar organic solvent, such as acetone, for 2–10 minutes.

When the reaction is complete, the obtained product is isolated as a salt of an inorganic or organic acid, preferably, as the hydrochloride.

DESCRIPTION OF THE PREFERRED EMBODIMENTS

EXAMPLE 1

14-acetyl-thiodaunorubicin hydrochloride 4.12 grams of 14-bromodaunomycin hydrobromide were suspended in 300 ml. of anhydrous acetone and treated with 3.3 g. of sodium thioacetate. After 5 minutes at room temperature, 400 ml. of 0.1 N hydrochloric acid were added to the reaction mixture and the solution was repeatedly extracted with chloroform (until the extracts were colorless) in order to eliminate the aglycones, and then with n-butyl alcohol. Several extractions were carried out until all of the colored products had passed into the organic layer. After concentration of the n-butyl alcohol under vacuum, 3 g. of crystalline 14-acetyl-thiodaunorubicin hydrochloride [yield: 85% — m.p. 189° (dec.)] were obtained.

EXAMPLE 2

14-benzoyl-thiodaunorubicin hydrochloride 4.1 grams of 14-bromodaunomycin were treated with 2.9 grams of sodium thiobenzoate under the same conditions as are described in Example 1. The yield amounted to 3.6 grams (yield: 87%) of 14-benzoyl-thiodaunorubicin hydrochloride, melting at 188° (dec.).

EXAMPLE 3

The reaction of 14-bromodaunomycin with the sodium salts of the following thioacids: thiopropionic, thiobutyric, thiooctanoic, thionicotinic and thiopyrazinoic, gave respectively 14-propanoyl-, 14-butanoyl-, 14-octanoyl-, 14-nicotinyl- and 14-pyrazinoyl- thiodaunorubicin which were isolated as the hydrochloride salts.

Pharmacology

Although the compounds of the present invention cannot be converted either to daunorubicin or to adriamycin in living organisms, they do exhibit a substantial and unexpected antitumor activity in experimental animals as shown in the following:

The activity of the compounds of Examples 1 and 2 on P. 388 leukemia in female mice was tested. The compounds were administered daily i.p. in aqueous solution on days 1 to 9.

The tests were performed under the auspices of the National Cancer Institute, Bethesda, Md., following the protocol set forth in Cancer Chemother., Rep. Part 3, Vol. 3, page 9 (1972).

| Compound | Dose (mg/kg) | T/C% | Survivors | T-C |
|---|---|---|---|---|
| Example 1 | 25.00 | 108 | 6/6 | −4.8 |
| | 12.50 | 146 | 6/6 | −4.5 |
| | 6.25 | 145 | 6/6 | −1.1 |
| | 3.13 | 136 | 6/6 | −0.8 |
| | 1.56 | 129 | 6/6 | −1.4 |
| Example 2 | 25.00 | | 5/6 | −5.5 |
| | 12.50 | 137 | 6/6 | −7.1 |
| | 6.25 | 131 | 6/6 | −2.1 |
| | 3.13 | 138 | 6/6 | −1.6 |
| | 1.56 | 128 | 6/6 | −1.4 |

T/C = Median Survival Time as percent of controls.
T-C = Weight difference (treated-controls).

Variations and modifications can, of course, be made without departing from the spirit and scope of the invention.

Having thus described our invention what we desire to secure by Letters Patent and hereby claim is:

1. A compound of the formula

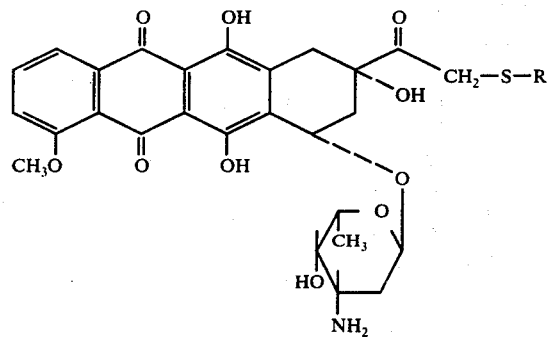

wherein R is the acyl radical of an aliphatic carboxylic acid having 2 to 8 carbon atoms, benzoic acid, nicotinic acid or pyrazinoic acid and the hydrochlorides thereof.

2. A compound according to claim 1, wherein R is acetyl propionyl, butanoyl or octanoyl.

3. A compound according to claim 1, which is 14-acetylthiodaunorubicin hydrochloride.

4. A compound according to claim 1, which is 14-benzoylthiodaunorubicin hydrochloride.

5. A compound according to claim 1, which is 14-propanoylthiodaunorubicin hydrochloride.

6. A compound according to claim 1, which is 14-butanoylthiodaunorubicin hydrochloride.

7. A compound according to claim 1, which is 14-octanoylthiodaunorubicin hydrochloride.

8. A compound according to claim 1, which is 14-nicotinoylthiodaunorubicin hydrochloride.

9. A compound according to claim 1, which is 14-pyrazinoylthiodaunorubicin hydrochloride.

10. A method of inhibiting the growth of $P_{388}$ leukemia which comprises intraperitoneally administering to a host afflicted therewith, a compound according to claim 1, in an amount sufficient to inhibit the growth of said tumor.

11. A method according to claim 10, wherein said compound is 14-acetyl-thiodaunorubicin or 14-benzoyl-thiodaunorubicin.

* * * * *